(12) United States Patent
Kuhn et al.

(10) Patent No.: US 6,783,555 B2
(45) Date of Patent: Aug. 31, 2004

(54) GAIT ORTHOSIS

(76) Inventors: Mark R. Kuhn, 4560 E. Todd St., Columbia, MO (US) 65201; Joshua A. Gilliland, 1188 SE. 180, Private Rd., Clinton, MO (US) 64735

(*) Notice: Subject to any disclaimer, the term of this patent is extended or adjusted under 35 U.S.C. 154(b) by 0 days.

(21) Appl. No.: 09/999,345

(22) Filed: Nov. 26, 2001

(65) Prior Publication Data

US 2002/0082711 A1 Jun. 27, 2002

Related U.S. Application Data

(60) Provisional application No. 60/243,968, filed on Oct. 27, 2000.

(51) Int. Cl.$^7$ .............................. A61F 2/74; A61F 5/00; A61H 3/00
(52) U.S. Cl. ................................. 623/27; 602/6; 482/66
(58) Field of Search ............................ 623/27, 28, 31, 623/32, 38, 30, 23; 602/5, 10, 16, 19; 482/66, 51

(56) References Cited

U.S. PATENT DOCUMENTS

| | | | | |
|---|---|---|---|---|
| 2,413,634 A | * | 12/1946 | Kolarik | 602/16 |
| 2,516,253 A | * | 7/1950 | Pieterick | 602/16 |
| 2,573,866 A | * | 11/1951 | Murphy | 602/16 |
| 4,489,717 A | * | 12/1984 | Moissonnier | 602/16 |
| 4,697,808 A | * | 10/1987 | Larson et al. | 482/51 |
| 4,946,156 A | | 8/1990 | Hart | |
| 4,957,103 A | | 9/1990 | Young et al. | |
| 4,964,628 A | | 10/1990 | Poplawski | |
| 5,020,790 A | | 6/1991 | Beard et al. | |
| 5,054,476 A | * | 10/1991 | Petrofsky et al. | 602/16 |
| 5,344,391 A | * | 9/1994 | Modglin | 602/24 |
| 5,556,373 A | * | 9/1996 | Motloch | 602/6 |
| 5,571,206 A | * | 11/1996 | Varn | 623/27 |
| 5,728,164 A | | 3/1998 | Ferrari et al. | |
| 6,494,853 B1 | * | 12/2002 | Rossi et al. | 602/16 |
| 6,540,703 B1 | * | 4/2003 | Lerman | 602/5 |

OTHER PUBLICATIONS

"Comparative Study of Conventional Hip–Knee–Ankle–Foot Orthoses Versus Reciprocating–Gait Orthoses for Children with High–Level Paraparesis" by Donald E. Katz, C.O.; Nasreen Haideri, M.E.; Kit Song, M.D.; and Phil Wyrick, M.S.; published in Journal of Pediatric Orthopaedics, vol. 17, No. 3, 1977 pp. 377–386.

"Reciprocating Gait Orthosis (RGO) A Historical Perspective" by Wallace Motloch, C.O., Published in the Journal of Proceedings for the 1999 Academy Scientific Symposium of the American Academy of Orthotists and Prosthetists.

"Walk Again: An Evaluation of the Walkabout Orthosis versus the Isocentric Reciprocal Gait Orthosis Paraplegics" summary of a Dec. 1996 joint research project conducted by the Prince Henry Hospital and the University of Sydney; final report to the Motor Accident Authority of New South Wales dated Dec., 1996, summary published at http://www.cchs.usyd.edu.au/rrc/wao.htm.

* cited by examiner

Primary Examiner—Corrine McDermott
Assistant Examiner—Alvin Stewart

(57) ABSTRACT

A unilateral or bilateral orthotic or prosthetic device that facilitates reciprocating ambulation by a human user is described. The reciprocating gait orthosis includes a torso vest securely positionable around the torso of the user, at least one torso joint coupled to the torso vest such that the torso joint is approximately adjacent to the user's natural waist, and at least one hip member that couples the torso joint and torso vest to a conventional leg support assembly at the hip joint approximately adjacent the user's natural hip joint. The leg support assembly is adapted to couple to the user's leg or to replace the human user's missing leg to provide the user stable support when the user is in an upright position.

20 Claims, 6 Drawing Sheets

GAIT ORTHOSIS

This application claims the benefit of the earlier filed U.S. Provisional Pat. App. Ser. No. 60/243,968, filed Oct. 27, 2000, entitled "Reciprocating Gait Orthosis" which is incorporated by reference for all purposes into this specification.

BACKGROUND OF THE INVENTION

1. Field of the Invention

The present invention relates to orthopedic appliances that help physically impaired individuals to stand and to walk. More specifically, the present invention facilitates standing and or ambulation and rehabilitation in patients otherwise unable to stand and to walk due to disability, injury, or disease.

2. Description of the Related Art

Many people are sufficiently physically impaired that they are unable to use their legs or have very limited or unbalanced use of their legs, and are thus conventionally restricted to self-powered mobility in the form of a wheelchair or stiff leg braces used with crutches or a walking frame which nearly surrounds the user. The problems and limitations faced by individuals relegated to wheelchairs are well known, and range from wheelchair related problems (e.g., building and facility access) to patient health related problems (e.g., osteoporosis and pressure sores). In response, a number of orthopedic appliances and devices have been developed to help these patients become more independent and ambulate without relying on a wheelchair.

One common device, well known in the art, is the hip-knee-ankle-foot orthosis, more commonly known as an HKAFO. HKAFOs comprise a body jacket or strap that includes a pelvic attachment connected, on each side, to a hip joint commonly having only one degree of freedom and a horizontal rotation axis. The hip joints have respective arms that are rigidly coupled, in their lower region, to the top of respective braces supporting the patient's thigh, leg, and foot. HKAFOs are commonly custom-designed and constructed by orthotists, using commercially-available locking joint and brace components, to accommodate each individual patient's size and physical needs. The hip joints and knee joints are unlocked when the patient using a HKAFO is seated. Using some form of assistance, the patient can then stand, lock the knee joints and hip joints, and then ambulate using a walker or crutches, employing either a swing-through or swivel gait.

Although still in common use, there are a number of problems with HKAFOs. The swing-through gait and swivel gait are both unnatural, and require a huge expenditure of energy. Even young and strong patients using a HKAFO tire quickly, and the high metabolic cost of using a HKAFO renders it impractical as a primary means of ambulation for many patients. Because the hips must remain locked to support the torso when the patient is upright, patients with some degree of hip flexor strength and mobility are prohibited from exercising and using their hip flexors to achieve a more natural gait.

The reciprocating gait orthosis ("RGO") was developed to address these concerns. RGOs are similar to HKAFOs, in that they typically comprise a body jacket that includes a pelvic attachment connected, on each side, to a hip joint. Like the HKAFO, the hip joints in the RGO have respective arms that are rigidly coupled, in their lower region, to the top of respective braces supporting the patient's thigh, leg, and foot. However, unlike the HKAFO, the hip joints in typical RGOs generally connect to one another across the body of the patient by sheathed control cables, a pivoting member, or the like, to transmit the mutual relative angular movements of the limbs. The mechanism connecting the hip joints in a RGO enables a patient to walk in a reciprocating gait, where the flexion of one leg is matched by the extension of the other leg. Therapists may find that RGOs are most appropriate for patients that have sufficient hip flexor mobility and strength to initiate a reciprocating gait, but even patients with no hip flexor power have successfully used RGOs. Some patients have found that the RGO offers easier negotiation of rough terrain, and most find the reciprocating gait to require a much lower expenditure of energy.

Nonetheless, current RGOs have limitations that can be problematic in some circumstances. Due to their more complex construction, current RGOs can be as much as 50% heavier than comparably-sized HKAFOs, and are consequently much more difficult for smaller patients and children to don. This extra weight and bulk makes the RGO more cumbersome and less comfortable than the HKAFO. One reason that some patients prefer the RGO over the HKAFO is the RGO's capability to enable a reciprocating gait, which requires a lower energy expenditure per unit of distance than the swing-through or swivel gait requires. However, this advantage is mitigated somewhat by the extra weight of the RGO.

RGOs are ordinarily much more expensive than HKAFOs, which is again problematic for children who require more frequent orthosis replacements as they outgrow their old devices. Although reciprocating mechanisms are commercially available, many orthotists who are comfortable designing and constructing HKAFOs for their patients are not comfortable constructing an RGO. Instead, orthotists may construct the knee-ankle-foot portion and assemble it with a torso-hip portion obtained from an RGO specialist.

Finally, some newly-injured patients who may initially require the level of support provided by traditional RGOs find that the forced reciprocating motion actually impedes rehabilitation as the patient recovers and regains strength and movement. Currently, therapists may switch these patients to progressively less-restrictive orthoses during the course of therapy, but this is expensive and hinders progress because the patient must learn to operate a new and unfamiliar apparatus. Permanently disabled individuals who are not in rehabilitation or recovery may prefer a device that enables a freer range of movement than traditional RGOs, even if using such a device requires additional support such as a walker, cane, or crutches because it does not force a reciprocating gait.

Due to these limitations, ordinarily a paraplegic patient's therapy is started using a HKAFO, rather than a RGO. If the patient does well with the HKAFO, the therapist may switch the patient to an RGO, depending upon the patient's motivation, familial support, financial support, and a number of other factors. Many patients that have used either an HKAFO or an RGO (or both) as a primary source for ambulation eventually abandon them in favor of a wheelchair, probably due to the limitations of both devices as described above. A need thus exists for an orthotic device that combines the advantages of prior art HKAFOs and RGOs, but eliminates the current problems inherent in each device. The present invention is such an orthotic device.

The present invention is a lightweight, simple, inexpensive orthosis that provides the support found in prior HKAFOs and RGOs, but enables a freer range of independent motion than current HKAFOs and RGOs. The present invention is therefore particularly suitable for children and smaller patients, and patients in rehabilitation that are recovering some degree of motion and strength. The present invention enables independent leg movement, and is thus highly useful for patients who do not need or want the forced scissors-type motion found in traditional RGOs.

The present invention is simpler in design, structure and operation than traditional RGOs, but provides patients with the capability of ambulation using a reciprocating, rather than a swing-through or swivel gait. The advantage offered by this combination of features is twofold: ambulation with a lower metabolic cost using a reciprocating gait, using a device as lightweight and comfortable as the HKAFO. The present invention allows, rather than forces, a reciprocating gait because the present invention allows the patient independent leg movement. Moreover, therapy using present invention is more economical than the traditional RGO-assisted or HKAFO followed by RGO-assisted therapy, for several reasons. First, the device itself provides the same function as a RGO, but is less expensive and can be fabricated by any experienced orthotist. Moreover, because the present invention also functions as a HKAFO, the therapist can start the patient's therapy with all joints locked, as though the patient were using a traditional HKAFO. Then, when the patient is ready to attempt a reciprocating gait, the waist joints can be unlocked to provide independent leg movement, without requiring a new device. Finally, the present invention adjusts to allow a recovering patient a greater degree of movement as his recovery progresses, thus eliminating or reducing the need for the recovering patient to switch to different orthoses to facilitate rehabilitation.

These and other features and advantages of the present invention will be apparent from the following detailed description and the accompanying drawings.

SUMMARY

The present invention is a method and apparatus that facilitates standing and or ambulation by a human user. The present invention includes a posterior torso support unit securely positionable around the posterior torso and extending mid way down gluteus maximus of the user, at least one waist joint coupled to the posterior torso support unit such that the waist joint is approximately adjacent to the user's natural waist, and at least one hip member that couples the waist joint and posterior torso support unit to a conventional leg support assembly at the hip joint. The leg support assembly is adapted to couple to the user's leg or to replace the human user's missing leg to provide the user stable support when the user is in an upright position. The top of the hip member couples to the waist joint, and the bottom of the hip member couples to the hip joint. The hip member is properly sized to place the hip joint approximately adjacent the user's natural hip joint.

The waist joint of the present invention can be a commercially available free motion hip joint with 180 degree stop, such as the free motion hip joint, Model No. 1025, commercially available from Becker Orthopedic. Alternatively, the waist joint may be a joint capable of being locked and unlocked by the user. Depending upon the needs of the user, the present invention may comprise a unilateral orthotic or prosthetic device that provides the user with support on only one side, in which case the present invention would include one waist joint, one hip joint, one hip member, and one leg support assembly. Alternatively, the present invention may comprise a bilateral orthotic or prosthetic device that provides support on both sides of the user's body. In the latter embodiment, the present invention could include right and left waist joints, right and left hip members, and right and left leg support assemblies, however, one practicing the present invention could include only one 0waist joint in a bilateral embodiment, if appropriate for a specific user.

BRIEF DESCRIPTION OF THE DRAWINGS

To further aid in understanding the invention, the attached drawings help illustrate specific features of the invention and the following is a brief description of the attached drawings.

DETAILED DESCRIPTION OF THE INVENTION

The present invention is a method and apparatus that facilitates standing and or ambulation by a human user. The present invention is a unilateral or bilateral orthotic or prosthetic device that includes a posterior torso support unit securely positionable around the posterior torso and extending mid way down the gluteus maximus of the user, at least one waist joint coupled to the posterior torso support unit such that the waist joint is approximately adjacent to the user's natural waist, and at least one hip member that couples the waist joint and posterior torso support unit to a conventional leg support assembly at the hip joint approximately adjacent the user's natural hip joint. The leg support assembly is adapted to couple to the user's leg or to replace the human user's missing leg to provide the user stable support when the user is in an upright position.

This disclosure describes numerous specific details, including specific hardware structures and specific commercially-available components, in order to provide a thorough understanding of the present invention. One skilled in the art will appreciate that one may practice the present invention without these specific details, and that equivalent structures well known in the art can be substituted without departing from the present invention. In addition, those skilled in the art will understand that in the embodiment of the present invention shown and described herein, the left side is a mirror image of the right side and the descriptive text and figures apply equally to both sides. However, after reading this disclosure or practicing the present invention, those skilled in the art will understand that this is not a limitation of the present invention. In other words, the present invention may be practiced in the context of an orthotic or prosthetic apparatus having two leg members wherein the left and right leg members are not mirror images of each other, according to the individual needs of the patient. Similarly, the present invention may be practiced in the context of an orthotic apparatus or prosthesis having only a single left or right leg member, according to the individual needs of the patient.

Figure 1:
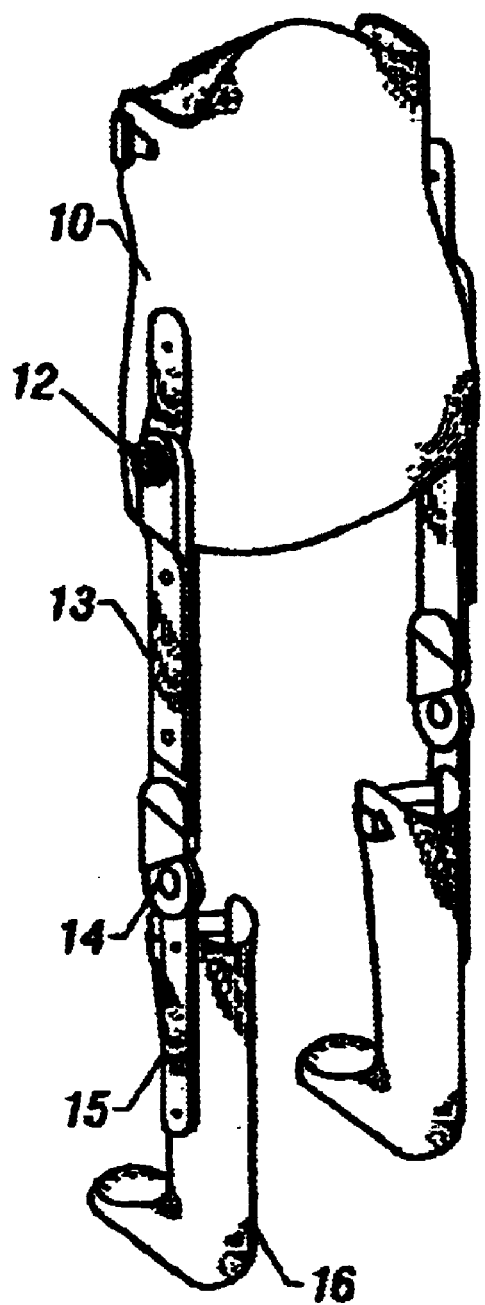
FIG. 1 shows a generic prior art hip-knee-ankle-foot orthosis (HKAFO).

FIG. 1 shows a generic HKAFO, comprising a conventional body jacket 10, hip joints 12, thigh members 13, knee joints 14, shin members 15, and combined lower leg/foot supports 16. To ambulate using the HKAFO, the patient rises from a seated position and locks the hip and knee joints 12, 14 to provide support for the torso. Using crutches, a walker or some other assistance, the patient can then move forward using a swing-through or swivel gait. Those skilled in the art are very familiar with HKAFOs and the various joint and support configurations available, and further detail regarding the structure of the HKAFO is not provided here. As described above, while HKAFOs are generally fairly lightweight and inexpensive to fabricate and deliver, the energy expenditure required to maintain the swing-through or swivel gait for any significant distance is high, limiting the usefulness of the HKAFO to young, strong, and highly motivated patients.

Figure 2:
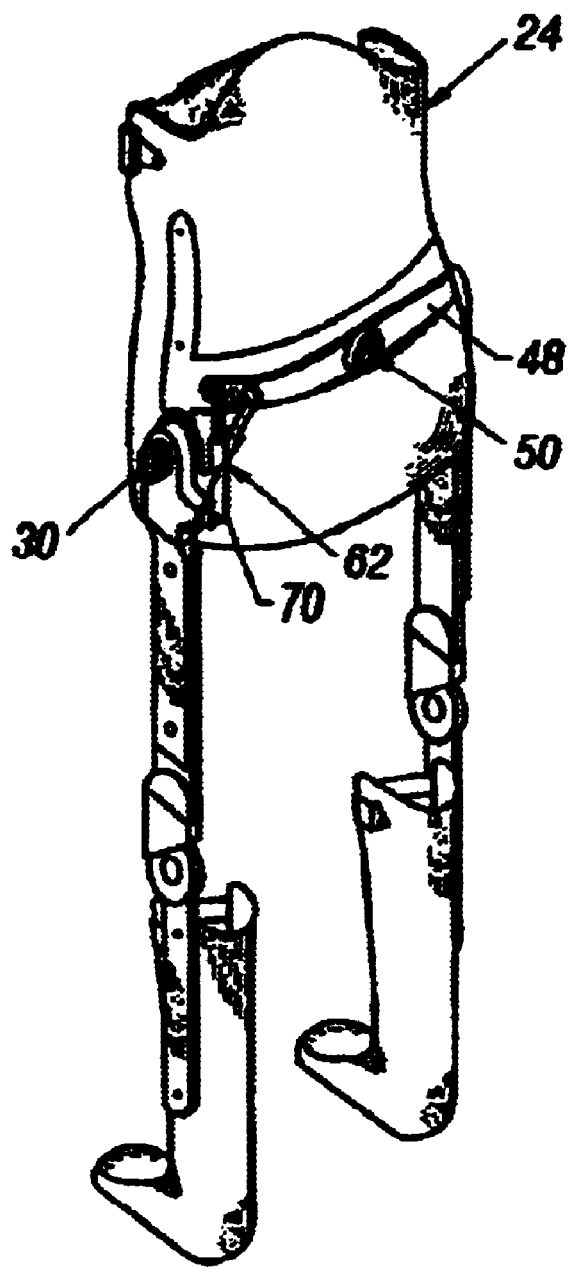
FIG. 2 shows a prior art reciprocating gait orthosis (RGO).

FIG. 2 shows a prior art RGO as described in U.S. Pat. No. 4,964,628, entitled "Hip-Reciprocating Apparatus," issued to Poplawski on Oct. 23, 1990. Poplawski's device includes a C-shaped pivoting member 48, which pivots about a pivot point 50 attached to the back of the conventional torso vest 24. Pivoting member 48 couples at each hip joint 30 to an adjustable tie rod assembly 62 that transfers the oppositional vertical motion of the ends of the C-shaped pivoting member 48 to oppositional horizontal motion of the leg members, thus producing a reciprocating, scissors-like movement of the leg members of the orthosis.

Figure 3:
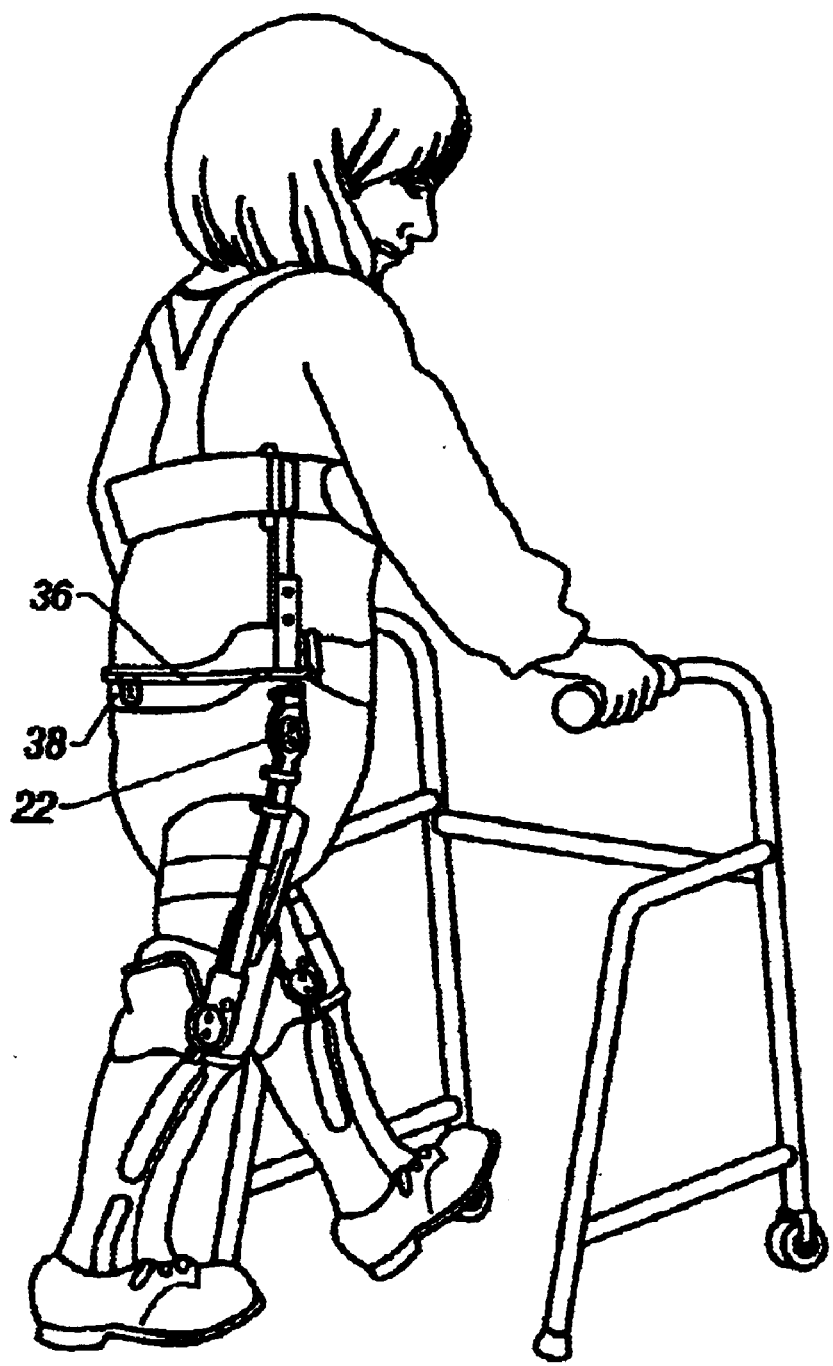
FIG. 3 shows a second prior art RGO.

FIG. 3 shows another prior art RGO, as described in U.S. Pat. No. 4,946,156, entitled "Orthosis or Prosthesis For Coordinating Limb Movement," issued to Hart on Aug. 7, 1990. Hart discloses a sheathed cable apparatus 36 coupled to each hip joint 22 and extending across the patient's back over a back band 38. Like Poplawski's device described above, Hart's cable apparatus 36 transfers motion between the leg members to produce a reciprocating gait.

As can be seen from both FIGS. 2 and 3, a patient using either Poplawski's or Hart's RGO is forced into a stiff, unnatural parade step by the reciprocating apparatus coupled to the hip joints and extending across the back of the patient's torso. Patients utilizing either of the prior art RGOs typically initiate a reciprocating gait by transferring their weight to one leg and leaning slightly backward at the torso. This forces the non-weight bearing leg to extend, and the patient then shifts his weight to the extended leg with sufficient forward momentum to cause the extended leg to rotate about the hip joint into a flexed position. This rotational movement is transferred via the pivoting plate or sheathed cable apparatus to the non-weight bearing leg, which is forced to extend forward as the weight-bearing leg rotates backward, at which point the patient shifts his weight to the newly extended leg. The patient continues forward in this manner, using momentum and repeated weight-shifting to achieve a reciprocating gait. The forced reciprocating motion produced by these devices is useful for patients who have no strength or independent motion in their hip flexors, and does not require the energy expenditure that the HKAFO requires. However, the forced reciprocation may overly limit some patients who have retained or are regaining movement and strength in the lower lumbar region and/or hip flexors. In addition, like other prior art RGOs, these devices are complex, expensive to fabricate and deliver, and so cumbersome that they are often too difficult for children and small patients to use, as described above.

Figure 4:
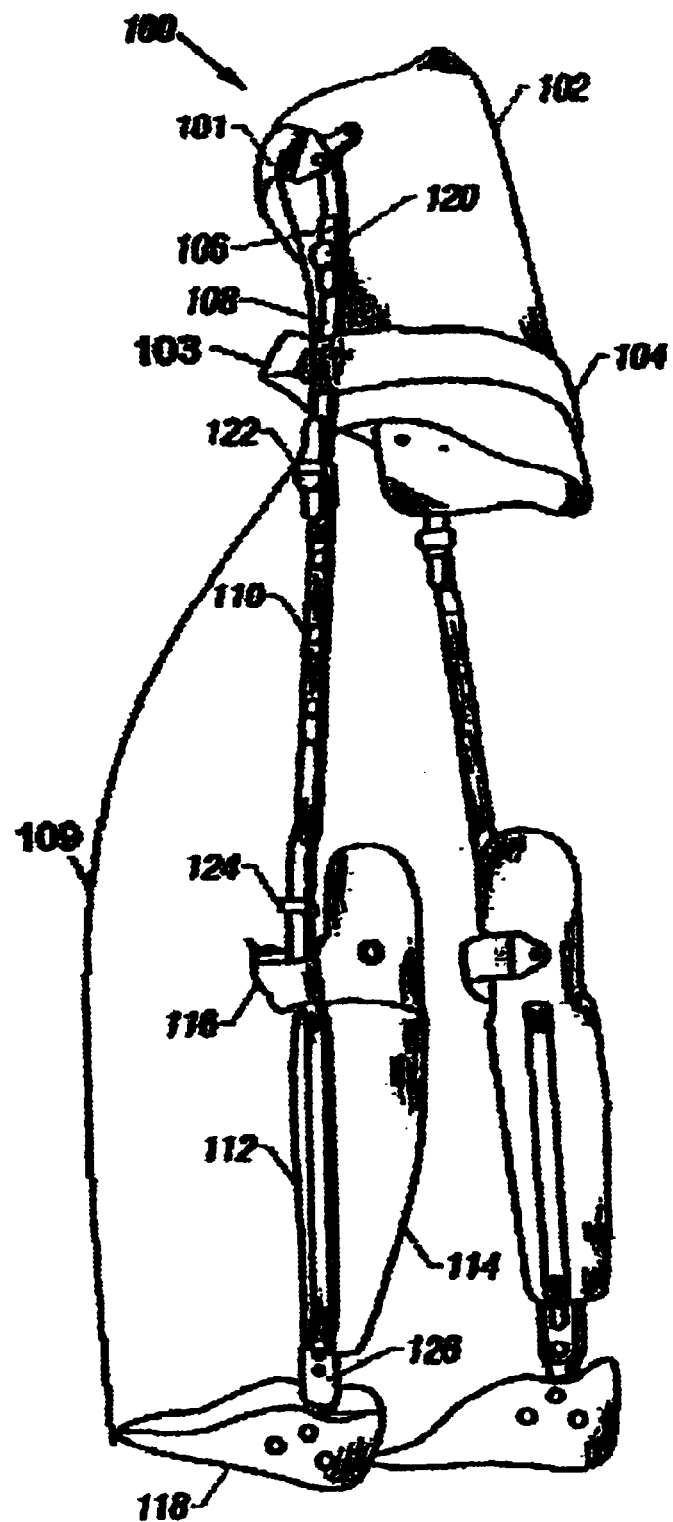
FIG. 4 shows the present invention, according to one embodiment.

The present invention overcomes these limitations of the prior art, by avoiding the use of a complex reciprocating apparatus that forces complimentary movement of the leg members, and by utilizing the simple construction approaches typically used in HKAFOs. The present invention enables, but does not force, a reciprocating gait by the novel use of an extra rotating joint above each hip joint. In addition, the joints utilized by the present invention are much simpler and lighter than the complex reciprocating hip joints used in prior art RGOs, and are capable of being locked or unlocked to accommodate the needs of the patient. FIG. 4 shows these features of the present invention, as described in more detail below.

As shown in FIG. 4, one embodiment of the present invention 100 includes a conventional posterior torso support unit 102, anterior chest strap 101, torso members 106, hip members 108, waist joints 120, anterior abdomen strap 103, posterior tension strap 104, and conventional leg assemblies 109 which include hip joints 122, thigh members 110, knee joints 124, shin members 112, lower leg supports 114, knee straps 116, ankle joints 126, and stirrups 118. In the embodiment shown in FIG. 4, posterior torso support unit 102 is made conventionally of a rigid padded structure, custom-cast to fit each individual user. Support unit 102 is positionable around the rear torso and extending mid way down gluteus maximus of the patient by conventional upper anterior chest straps 101, and lower anterior abdominal straps 103 that extends across the front of the patient's torso. Straps 101, 103, and 104 are preferably constructed of nylon webbing and Velcro for maximum patient comfort and ease of use, but any lightweight material and convenient fastening system may be substituted. As shown in FIG. 4, the posterior tension strap 104 extends over hip member 108 thus capturing hip member 108 relatively tightly against posterior torso support unit 102.

Figure 5:
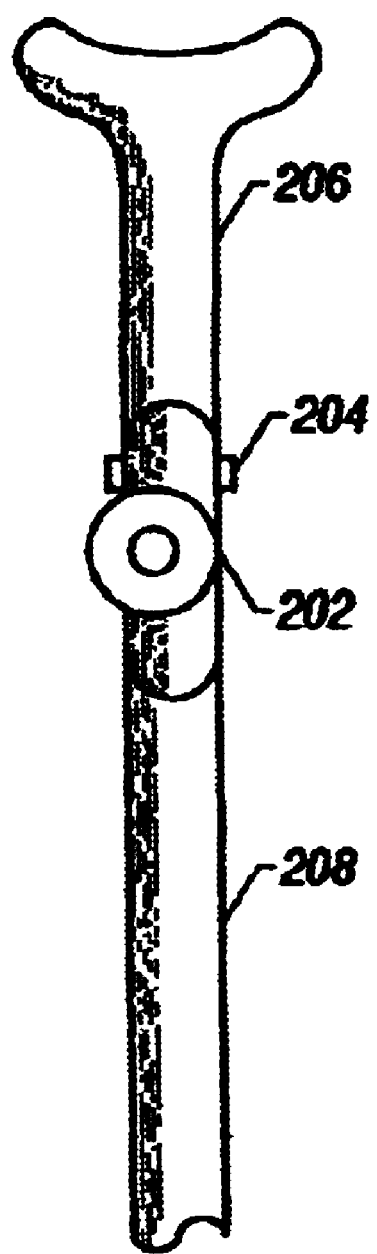
FIG. 5 shows the major elements of a typical commercially-available hip joint used in orthotic devices.

Leg assemblies 109 are conventional and comprise components that are well known in the art. In a preferred embodiment, hip joints 122 comprise commercially-available stainless steel droplock hip joints such as the left and right modified ring lock hip joint, Model No. 1022, commercially available from Becker Orthopedic, 635 Executive Drive, Troy, Mich., 48083-4576, and knee joints 124 comprise commercially-available stainless steel droplock knee joints such as the left and right modified ring lock knee joint, Model No. 1002, also available from Becker Orthopedic. FIG. 5 shows that a typical, commercially-available locking hip joint such as Becker's Model No. 1022 ring long hip joint includes four major elements: the joint subassembly element 202, the locking element 204, the upper upright member 206, and the lower upright member 208. Those skilled in the art are very familiar with orthosis construction techniques utilizing commercially available joints and their upright members, and the typical leg assemblies 109 shown in FIG. 4 are constructed using these techniques. For example, in accordance with standard, well-known HKAFO and RGO construction techniques, thigh members 110 may be formed by longitudinally aligning and permanently coupling the lower upright of hip joint 122 to the upper upright of knee joint 124, such that the knee joint 124 is properly positioned adjacent to and alongside the user's natural knee joint or at the approximate location that the user's knee joint should be, if the device is being used as a prosthesis. Those skilled in the art will understand that one practicing the present invention may substitute other commercially available or custom-designed hip and knee joints and uprights, or their equivalents, according to the needs of the patient, without departing from the present invention.

Like the hip and knee joints and thigh members described above, ankle joints 126 and stirrups 118 are conventional, well known in the art, and equivalent to various commercially available ankle joints and stirrups, according to the needs of the patient. Shin members 112 are constructed conventionally by coupling the knee joint 124 lower uprights to the ankle joint 126 upper uprights or to the rigid lower leg supports 114. Likewise, lower leg supports 114 and stirrups 118 are preferably made conventionally of a smooth thermoplastic or carbon graphite laminate, each custom-cast to fit each individual patient. In the embodiment shown in FIG. 4, lower leg supports 114 are securely positioned behind the patient's calves by knee straps 116. While the leg assemblies 109 shown in FIG. 4 and described above are constructed using techniques and components well known to orthotists experienced in designing and construction custom-made HKAFOs and RGOs, those skilled in the art will understand that embodiments having different leg assembly arrangements will not depart from the present invention.

Figure 6:
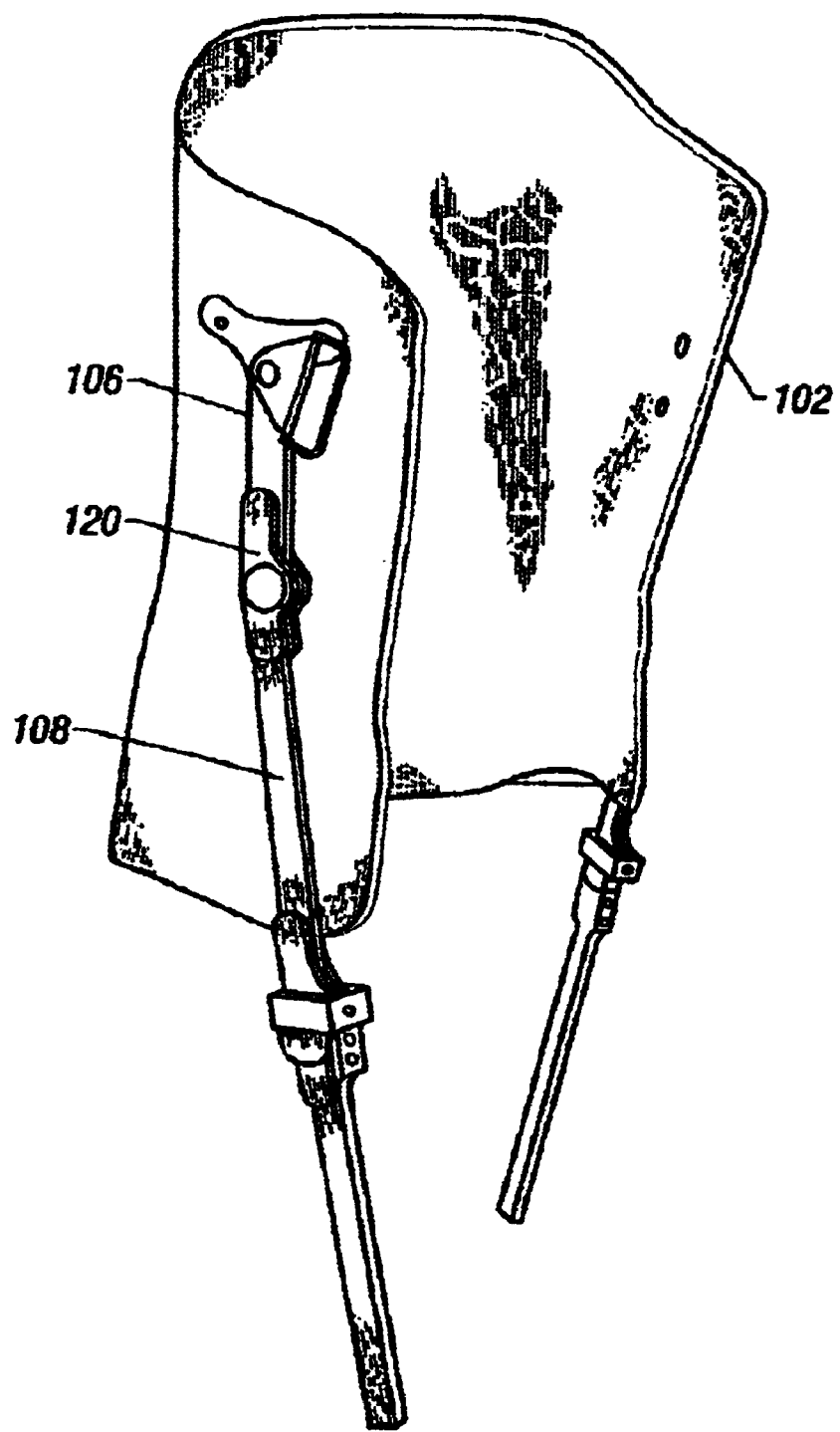
FIG. 6 is a closeup view of the posterior torso support unit section and waist joint of the present invention, according to one embodiment.

FIG. 6 is a closeup view of one side of the torso section of the present invention, showing support unit 102, torso member 106, waist joint 120, hip member 108, and the top portion of a leg assembly 109 comprising a hip joint 122. In a preferred embodiment, waist joint 120 comprises a stainless steel free motion joint with 180 degree stop, such as the free motion hip joint, Model No. 1025, commercially available from Becker Orthopedic. Torso member 106 comprises the Y-shaped upright that forms the upper part of Becker's Model No. 1025 free motion hip joint. Torso member 106 is permanently coupled to posterior torso support unit 102, positioned to insure that when the posterior torso support unit 102 is properly positioned on the user's body, the waist joint 120 is located at the user's side, midline on the body, approximately adjacent the natural waist just below the ribcage. After reading this specification and/or practicing the present invention, those skilled in the art will recognize that the ideal location of waist joint 120 may vary according to the needs and structure of the patient, but that waist joint 120 must be approximately midline on the body, above hip joint 122, and must not interfere with posterior tension strap 104.

Those skilled in the art will understand that one practicing the present invention may substitute another commercially available or custom-designed joint for the Becker Orthopedic joint and upright that comprises waist joint 120 and torso member 106 described above, according to the needs of the patient, without departing from the present invention. For example, in the embodiment shown in FIG. 6, the waist joint 120 does not include a locking device. In another embodiment, the waist joint 120 is capable of being locked, allowing the present invention to function similar to a standard HKAFO. Those skilled in the art will understand that the selection of a locking versus a non-locking joint will be dictated by the individual needs of the patient.

In the embodiment shown in FIGS. 4 and 6, hip member 108 comprises the lower upright of Becker's Model No. 1025 free motion hip joint, modified at the lower end to enable hip member 108 to be permanently coupled to a commercially-available hip joint 122 in the same manner that the upper upright of commercially-available hip joint 122 would ordinarily be coupled to the joint subassembly element. In other words, one practicing the present invention using a Becker Orthopedic model 1022 modified ring lock hip joint for hip joint 122 and a Becker Orthopedic model 1025 free motion hip joint for the waist joint 120 would not use the Y-shaped upper upright that Becker ordinarily offers for use with the Becker model 1022 hip joint. Instead, the lower upright of the Becker model 1025 joint is cut to a length that places hip joint 122 at the proper position adjacent the user's natural hip joint when the lower upright is coupled to the joint subassembly element that comprises hip joint 122.

A patient using the present invention might initially require all of the joints to be locked in order to remain in a standing position or to walk. In this configuration, if the orthotist has utilized locking waist joints, the present invention functions as a standard HKAFO and the patient can ambulate using a swing-through gait. As the patient becomes stronger and more proficient, the therapist may unlock the waist joints and the patient may begin ambulating with a reciprocating gait. While the present invention is most useful for patients who have retained or are regaining some degree of hip flexor strength, even patients that have no movement or strength in one or both hip flexors can master a reciprocating gait using the present invention.

Patients utilizing the present invention typically initiate a reciprocating gait with the hip joints 122 locked and the waist joints 120 unlocked. The patient transfers his or her weight to one leg and leans slightly backward at the torso. The rigid posterior torso support unit 102 forces the non-weight bearing leg to extend, and the patient then shifts his weight to the extended leg with sufficient forward momentum to cause the extended leg to rotate about the waist joint into a flexed position. The posterior tension strap 104 prevents unwanted lateral movement in the patient's hip joint, and provides sufficient friction against the posterior torso support unit 102 to continue to support the patient upright. As the patient shifts his weight onto the initially forward extended leg the original weight-bearing leg becomes unweighted, the patient leans backward at the torso, and the now-unweighted leg extends forward. The patient repeats this process to achieve a more natural reciprocating gait.

As the patient recovers strength and movement, the present invention also provides the therapist the ability to unlock individual joints as appropriate to provide the patient with the degree of freedom and support dictated by the patient's individual needs. For example, patients who have or are regaining strength in their hip flexors can unlock one or both hip joints and use their hip flexors, in combination with the weight-shifting technique described above, to achieve a reciprocating gait. Similarly, the therapist might initiate each session with one or more knee joints unlocked for a patient who is gaining or regaining use of the quadriceps. When the patient tires during the course of a therapy session, the hip joints or knee joints can be then be relocked to provide stability and support as required. The present invention is thus unlike prior art devices, in that it can accommodate the patient's changing needs through the course of the patient's recovery. The present invention eliminates the need for a patient to progress from restrictive to less-restrictive devices through the course of therapy, eliminating the expense of multiple devices and the recovery delay that can occur while the patient familiarizes himself with a new device.

To summarize, the present invention is a unilateral or bilateral orthotic or prosthetic apparatus and method that facilitates standing and or ambulation by a human user. The present invention includes a posterior torso support unit securely positionable around the posterior torso and extending mid way down gluteus maximus of the user, at least one waist joint coupled to the posterior torso support unit such that the waist joint is approximately adjacent to the user's natural waist, and at least one hip member that couples the waist joint and posterior torso support unit to a conventional leg support assembly at the hip joint. The leg support assembly is adapted to couple to the user's leg or to replace the human user's missing leg to provide the user stable support when the user is in an upright position. The top of the hip member couples to the waist joint, and the bottom of the hip member couples to the hip joint. The hip member is properly sized to place the hip joint approximately adjacent the user's natural hip joint.

The waist joint of the present invention can be a commercially available free motion hip joint with 180 degree stop, such as the free motion hip joint, Model No. 1025, commercially available from Becker Orthopedic. Alternatively, the waist joint may be a joint capable of being locked and unlocked by the user. Depending upon the needs of the user, the present invention may comprise a unilateral orthotic or prosthetic device that provides the user with support on only one side, in which case the present invention would include one waist joint, one hip joint, one hip member, and one leg support assembly. Alternatively, the present invention may comprise a bilateral orthotic or prosthetic device that provides support on both sides of the user's body. In the latter embodiment, the present invention could include right and left waist joints, right and left hip members, and right and left leg support assemblies, however, one practicing the present invention could include only one waist joint in a bilateral embodiment, if appropriate for a specific user.

Other embodiments of the invention will be apparent to those skilled in the art after considering this specification or practicing the disclosed invention. The specification and examples above are exemplary only, with the true scope of the invention being indicated by the following claims.

We claim the following invention:

1. An apparatus for facilitating standing and or ambulation by a human user, comprising: a posterior torso support unit securely positionable around the posterior torso and extending midway down gluteus maximus of the human user;
   at least one waist joint coupled to said posterior torso support unit approximately midline on the body of the human user and adjacent to the natural waist of the human user, said waist joint couples to said posterior torso support unit by a torso member, proximal to waist joint, rigidly coupled to said posterior torso support unit and to said waist joint;
   at least one hip member coupled to said waist joint with posterior tension strap attached to distal portion of posterior torso support unit surrounding one or both sides of said hip member and to at least one leg support assembly adapted to couple to the human user's leg or to replace the human user's missing leg to stably support the human user in an upright position, said leg support assembly further comprises a hip joint, said hip member is sized to extend from said waist joint to said hip joint approximately adjacent the natural hip of the human user.

2. The apparatus of claim 1, wherein said waist joint further comprises a joint capable of being locked and unlocked by the human user.

3. The apparatus of claim 1, wherein said waist joint further comprises a commercially available free motion hip joint with 180 degree stop.

4. The apparatus of claim 1, further comprising two waist joints, one posterior tension strap, two hip members, two hip joints, and two leg support assemblies.

5. The system of claim 1, further comprising two waist joints, one posterior tension strap, two hip members, two hip joints, and two leg support assemblies.

6. A system that facilitates standing and or ambulation by a human user, comprising:
   a posterior torso support unit securely positionable around the posterior torso and extending midway down gluteus maximus of the human user; at least one waist joint coupled to said posterior torso support unit approximately midline on the body of the human user and adjacent to the natural waist of the human user, said waist joint couples to said posterior torso support unit by a torso member, proximal to waist joint, rigidly coupled to said posterior torso support unit and to said waist joint;
   at least one hip member coupled to said waist joint with posterior tension strap attached to distal portion of posterior torso support unit surrounding one or both sides of said hip member and to at least one leg support assembly adapted to couple to the human user's leg or to replace the human user's missing leg to stably support the human user in an upright position, said leg support assembly further comprises a hip joint, said hip member is sized to extend from said waist joint to said hip joint approximately adjacent the natural hip of the human user.

7. The system of claim 6, wherein said waist joint further comprises a joint capable of being locked and unlocked by the human user.

8. The system of claim 6, wherein said waist joint further comprises a commercially available free motion hip joint with 180 degree stop.

9. A method of making an apparatus for facilitating standing and or ambulation by a human user, comprising:
   providing a posterior torso support unit securely positionable around the posterior torso and extending midway down gluteus maximus of the human user;
   providing at least one waist joint coupled to said posterior torso support unit approximately midline on the body of the human user and adjacent to the natural waist of the human user, said waist joint couples to said posterior torso support unit by a torso member, proximal to waist joint, rigidly coupled to said posterior torso support unit and to said waist joint;
   coupling at least one hip member to said waist joint with posterior tension strap attached to distal portion of posterior torso support unit surrounding one or both sides of said hip member and to at least one leg support assembly adapted to couple to the human user's leg or to replace the human user's missing leg to stably support the human user in an upright position, said leg support assembly further comprises a hip joint, said hip member is sized to extend from said waist joint to said hip joint approximately adjacent the natural hip of the human user.

10. The method of claim 9, wherein said waist joint further comprises a joint capable of being locked and unlocked by the human user.

11. The method of claim 9, wherein said waist joint further comprises a commercially available free motion hip joint with 180 degree stop.

12. The method of claim 9, further comprising providing two waist joints, one posterior tension strap, two hip members, two hip joints, and two leg support assemblies.

13. A method of using an apparatus that facilitates standing and or ambulation by a human user, comprising:
   positioning a posterior torso support unit securely around the posterior torso and extending midway down gluteus maximus of the human user, wherein said posterior torso support unit further comprises at least one waist joint coupled to said posterior torso support unit approximately midline on the body of the human user and adjacent to the natural waist of the human user, said waist joint couples to said posterior torso support unit by a torso member, proximal to waist joint, rigidly coupled to said posterior torso support unit and to said waist joint; and coupling at least one leg support assembly to the human user's leg or in such a manner to replace the human user's missing leg, such that said leg support assembly stably supports the human user in an upright position, said leg support assembly further comprises a hip joint that couples to said waist joint by a hip member sized to extend from said waist joint to said hip joint approximately adjacent the natural hip of the human user.

14. The method of claim 13, wherein said waist joint further comprises a joint capable of being locked and unlocked by the human user.

15. The method of claim 13, wherein said waist joint further comprises a commercially available free motion hip joint with 180 decree stop.

16. The method of claim 13, further comprising providing two waist joints, one posterior tension strap, two hip members, two hip joints, and two leg support assemblies.

17. An apparatus that facilitates standing and or ambulation by a human user, comprising: a posterior torso support unit securely positionable around the posterior torso and extending midway down the gluteus maximus of the human user;

right and left waist joints wherein each said waist joint comprises one of the following: a joint capable of being locked and unlocked by the human user; or a free motion with 180 decree stop hip joint, said right and left waist joints are coupled to said posterior torso support unit approximately midline on the body of the human user and adjacent to the natural waist of the human user by right and left torso members, proximal to waist joint, rigidly coupled to said posterior torso support unit; and right and left hip members coupled respectively to said right and left waist joints with posterior tension strap attached to distal portion of posterior torso support unit surrounding one or both sides of said hip members and to right and left leg support assemblies, wherein each said leg support assembly is adapted to couple to the human user's leg or to replace the human users missing leg to stably support the human user in an upright position, said right leg support assembly further comprises a right hip joint, and said left leg support assembly further comprises a left hip joint, said right and left hip members are sized to extend from said right and left waist joints to said right and left hip joints such that said right and left hip joints are located approximately adjacent the natural right and left hip joints of the human user.

18. A system that facilitates standing and or ambulation by a human user, comprising: a posterior torso support unit securely positionable around the posterior torso and extending midway down the gluteus maximus of the human user;

right and left waist joints wherein each said waist joint comprises one of the following: a joint capable of being locked and unlocked by the human user; or a free motion with 180 degree stop hip joint, said right and left waist joints are coupled to said posterior torso support unit approximately midline on the body of the human user and adjacent to the natural waist of the human user by right and left torso members, proximal to waist joint, rigidly coupled to said posterior torso support unit; and right and left hip members coupled respectively to said right and left waist joints with posterior tension strap attached to distal portion of posterior torso support unit surrounding one or both sides of said hip members and to right and left leg support assemblies, wherein each said leg support assembly is adapted to couple to the human users leg or to replace the human user's missing leg to stably support the human user in an upright position, said right leg support assembly further comprises a right hip joint, and said left leg support assembly further comprises a left hip joint, said right and left hip members are sized to extend from said right and left waist joints to said right and left hip joints such that said right and left hip joints are located approximately adjacent the natural right and left hip joints of the human user.

19. A method of making an apparatus that facilitates standing and or ambulation by a human user, comprising: providing a posterior torso support unit securely positionable around the posterior torso and extending midway down the gluteus maximus of the human user;

providing right and left waist joints wherein each said waist joint comprises one of the following: a joint capable of being locked and unlocked by the human user; or a free motion with 180 decree stop hip joint, said right and left waist joints are coupled to said posterior torso support unit approximately midline on the body of the human user and adjacent to the natural waist of the human user by right and left torso members, proximal to waist joint, rigidly coupled to said posterior torso support unit; and coupling right and left hip members to said right and left waist joints with posterior tension strap attached to distal portion of posterior torso support unit surrounding one or both sides of said hip members respectively and to right and left leg support assemblies respectively, wherein each said leg support assembly is adapted to couple to the human user's leg or to replace the human user's missing leg to stably support the human user in an upright position, said right leg support assembly further comprises a right hip joint, and said left leg support assembly further comprises a left hip joint, said right and left hip members are sized to extend from said right and left waist joints to said right and left hip joints such that said right and left hip joints are located approximately adjacent the natural right and left hip joints of the human user.

20. A method of using an apparatus that facilitates standing and or ambulation by a human user, comprising: securely positioning a posterior torso support unit around the posterior torso and extending midway down the gluteus maximus of the human user, said posterior torso support unit further comprises right and left waist joints wherein each said waist joint comprises one of the following: a joint capable of being locked and unlocked by the human user; or a free motion with 180 degree stop hip joint, said right and left waist joints are coupled to said posterior torso support unit approximately midline on the body of the human user and adjacent to the natural waist of the human user by right and left torso members, proximal to waist joint, rigidly coupled to said posterior torso support unit; and coupling right and left leg support assemblies to the human users right and left legs, respectively, or to the human user in such a manner as to replace the human user's missing leg or legs to stably support the human user in an upright position, said right leg support assembly further comprises a right hip joint coupled to said right waist joint by a right hip member, said right hip member is sized to extend from said right waist joint to said right hip joint such that said right hip joint is located approximately adjacent the natural right hip joint of the human user; said left leg support assembly further comprises a left hip joint coupled to said left waist joint by a left hip member, said left hip member is sized to extend from said left waist joint to said left hip joint such that said left hip joint is located approximately adjacent the natural left hip joint of the human user.

* * * * *